United States Patent
Kobayashi

(10) Patent No.: US 7,623,150 B2
(45) Date of Patent: Nov. 24, 2009

(54) ELECTRONIC ENDOSCOPE

(75) Inventor: Hiroyuki Kobayashi, Saitama (JP)

(73) Assignee: Hoya Corporation, Tokyo (JP)

( * ) Notice: Subject to any disclaimer, the term of this patent is extended or adjusted under 35 U.S.C. 154(b) by 883 days.

(21) Appl. No.: 10/737,895

(22) Filed: Dec. 18, 2003

(65) Prior Publication Data
US 2004/0125203 A1  Jul. 1, 2004

(30) Foreign Application Priority Data
Dec. 19, 2002  (JP) ............... P2002-368402

(51) Int. Cl.
H04N 13/00 (2006.01)
H04N 5/335 (2006.01)

(52) U.S. Cl. .................. 348/45; 348/222.1

(58) Field of Classification Search .............. 348/65, 348/69, 68, 71, 61, 645, 649, 230, 73, 75, 348/222.1, 45, 600, 589, 705, 72, 625; 600/160, 600/180, 109, 101, 181
See application file for complete search history.

(56) References Cited

U.S. PATENT DOCUMENTS

| 5,269,289 | A | * | 12/1993 | Takehana et al. ........... 600/109 |
| 5,408,263 | A | | 4/1995 | Kikuchi et al. |
| 5,864,361 | A | | 1/1999 | Sekiya et al. |
| 6,080,104 | A | | 6/2000 | Ozawa et al. |
| 6,414,710 | B1 | | 7/2002 | Takahashi et al. |
| 6,473,116 | B1 | * | 10/2002 | Takahashi ................ 348/65 |
| 7,070,560 | B2 | * | 7/2006 | Takahashi ............... 600/178 |
| 2001/0007468 | A1 | | 7/2001 | Sugimoto et al. |
| 2002/0196335 | A1 | | 12/2002 | Ozawa |
| 2003/0001952 | A1 | | 1/2003 | Iida et al. |
| 2003/0030722 | A1 | | 2/2003 | Ozawa et al. |
| 2003/0076412 | A1 | | 4/2003 | Ozawa |
| 2005/0068427 | A1 | * | 3/2005 | Sudo et al. ............ 348/222.1 |

FOREIGN PATENT DOCUMENTS

| JP | 5-228110 | 9/1993 |
| JP | 6-090900 A | 4/1994 |
| JP | 2000-209605 | 7/2000 |
| JP | 2000-221417 | 8/2000 |
| JP | 2000-354240 | 12/2000 |
| JP | 2001-154232 | 6/2001 |

OTHER PUBLICATIONS

English language Abstract of JP 6-090900 A.
English language Abstract of JP 2000-354240, Dec. 19, 2000.
English language Abstract of JP 2001-154232, Jun. 8, 2001.
English language Abstract of JP 5-228110, Sep. 7, 1993.
English language Abstract of JP 2000-209605, Jul. 28, 2000.

* cited by examiner

Primary Examiner—Behrooz Senfi
(74) Attorney, Agent, or Firm—Greenblum & Bernstein PLC

(57) ABSTRACT

Analog pixel signals, which are read out from an image sensor, are subjected to predetermined signal processes, and are converted to digital pixel signals by an A/D converter. The digital pixel signals are separated to RGB signals. The RGB signals are multiplied by a predetermined color matrix coefficient. After that, luminance signals are extracted from the RGB signals. A light adjusting control signal for adjusting the quantity of light is calculated based on the luminance signals. The color matrix coefficient is changed based on the light adjusting control signal.

7 Claims, 5 Drawing Sheets

ELECTRONIC ENDOSCOPE

BACKGROUND OF THE INVENTION

1. Field of the Invention

The present invention relates to color reproduction of an object of view in an electronic endoscope.

2. Description of the Related Art

Conventionally, there is an electronic endoscope which captures an object image by the color chip method, using a color CCD. An insert portion of the electronic endoscope is inserted into a body of a patient. A fiber bundle (light guide), which is a bundle of extra fine optical fibers, is penetrated through the insert portion. White illumination light, which is supplied from a light source device, is led to the tip of the insert portion by the light guide, and illuminates an object of view from the tip. The color CCD is provided with color chip filters having complementary colors (magenta, yellow, cyan, and green) which are arranged mosaically. Light reflected by the object is imaged on an image capturing plane of the color CCD through objective lenses. The imaged optical image is subjected to photoelectric conversion by the color CCD, whereby an image signal is output from the color CCD.

The electronic endoscope is connected to an image processing device. After the image signal is output from the color CCD, it is subjected to predetermined image processing in the image processing device. The image signal is then subjected to a multiplying operation in which it is multiplied by a predetermined matrix coefficient, and then the image signal is converted to an RGB signal which includes a red color component, green color component, and blue color component. A TV-monitor is connected to the image processing device. The RGB signal which is converted in the image processing device, is output to the TV-monitor. Consequently, a picture of the object is produced on a display of the TV-monitor.

Generally, a xenon lamp, a halogen lamp, a metal halide lamp, and so on, can be utilized as a light source of the above-mentioned white illumination light. These lamps have different spectral characteristics. Accordingly, when the picture is produced on the display of the TV-monitor after the processing by the image processing device, the color reproduction of the picture depends upon the light source. Therefore, the matrix coefficient which is used in the RGB conversion operation is adjusted in accordance with light source of the illumination light so that good color reproduction can be obtained.

Spectral sensitivity of complementary color filters of color CCDs overlaps at some frequencies. Accordingly, difference in the luminance brightness between some portions of the optical image of the object may cause discordance in the saturation of the complementary color filter. Due to this discordance, some colors of the object produced on the monitor may differ from their real color. Namely, even though the matrix coefficient is adjusted based on the kind of light source, luminance brightness conditions of the optical image may prevent the colors of some portions of the object from being precisely reproduced.

SUMMARY OF THE INVENTION

Therefore, an object of the present invention is to obtain the best color reproduction at all times in an electronic endoscope.

In accordance with an aspect of the present invention, there is provided an electronic endoscope comprising a device that carries out photoelectric conversion of an image of an object of view and outputs pixel signals of the object image; a converter that converts the pixel signals to color component signals for video signals; a color adjuster that adjusts colors of the color component signals by multiplying a predetermined matrix coefficient; a light adjusting controller that calculates a luminance of the object image from the color component signals, the colors of which are adjusted, and creates a control signal for adjusting the quantity of illumination light; a color adjusting controller that changes the predetermined matrix coefficient based on the control signal created by the light adjusting controller.

Preferably, the color adjuster compares the control signal with a predetermined threshold, and selects one matrix coefficient from a plurality of matrix coefficients based on the comparison. The plurality of matrix coefficients have at least one different element.

Optionally, the color adjusting controller changes at least one element of the predetermined matrix coefficient based on a predetermined expression using the control signal.

Optionally, the light adjusting controller obtains the control signal by calculating an average value of luminance of all pixels which compose the object image and a peak value of luminance of pixels which are in the central portion of the object image. Preferably, the light adjusting controller weights each of the average values and the peak value.

Optionally, the color adjusting controller changes a plurality of elements, of the predetermined matrix coefficient, which relate to one color component.

Optionally, the color adjusting controller changes a plurality of elements, of the predetermined matrix coefficient, which relate to a plurality of color components.

According to the present invention, the matrix coefficient, which is used for color adjusting the color component signals, is changed based on the control signal which is created from the luminance of the object image. Accordingly, good color reproduction can be obtained at all times in accordance with the luminance of the object.

BRIEF DESCRIPTION OF THE DRAWINGS

The objects of the present invention will be better understood from the following description, with reference to the accompanying drawings, in which.

DESCRIPTION OF THE PREFERRED EMBODIMENTS

Figure 1:
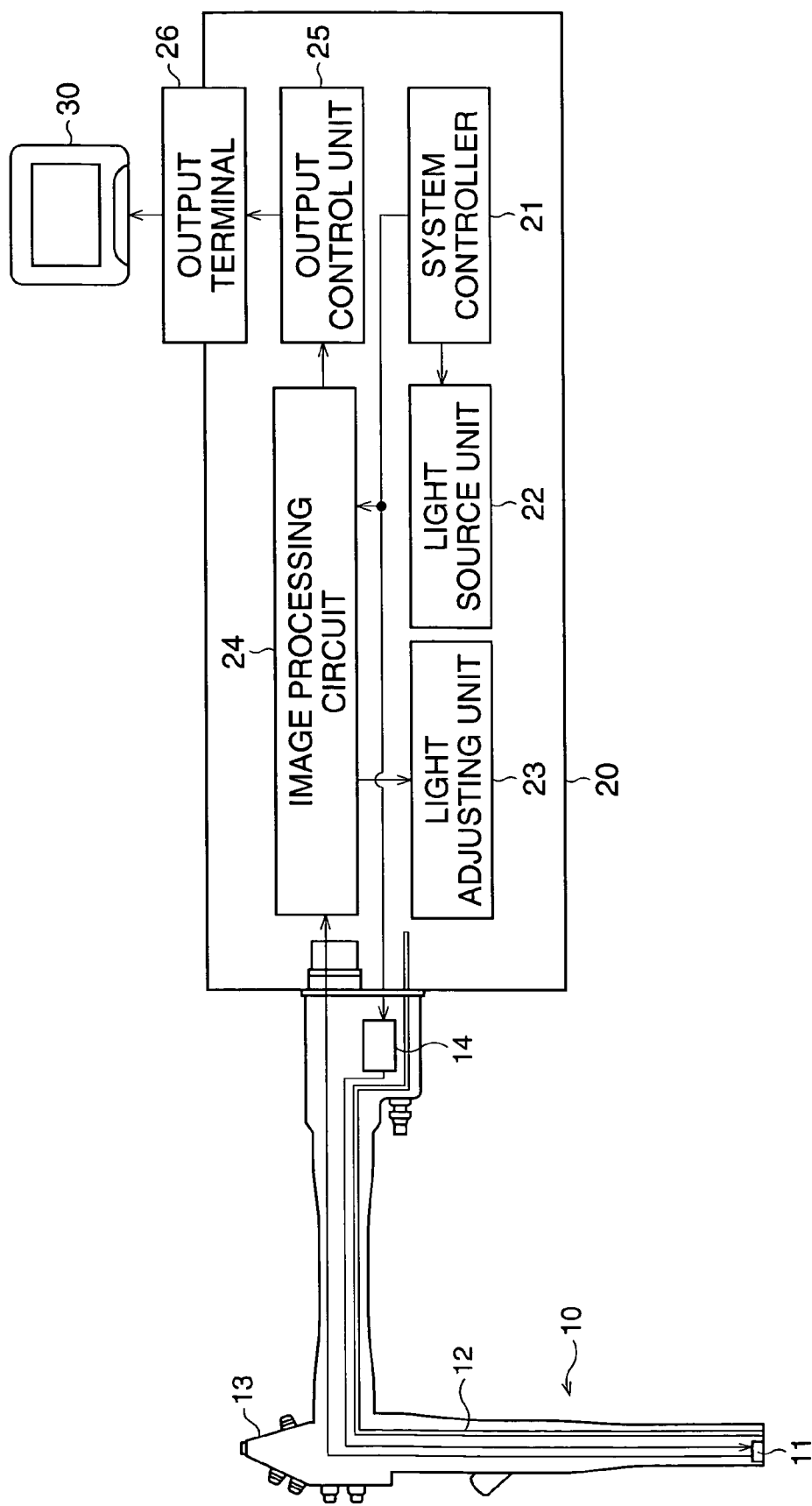
FIG. 1 is a block diagram of an electronic endoscope, to which a first embodiment according to the present invention is applied.

The present invention will now be described with reference to embodiments shown in the drawings.

FIG. 1 is a block diagram of an electronic endoscope to which a first embodiment according to the present invention is applied. An electronic scope 10 includes a flexible tube. The scope 10 is connected to an image-signal processing device 20 in such a manner that the scope 10 is attachable to and detachable from the device 20. An image sensor 11, which includes an objective optical system and a CCD image sensor, is provided at the tip of the scope 10. A light guide 12 passes through the scope 10. An emitting end of the light guide 12 is arranged at the distal end of the scope 10. Operating buttons are provided on a control portion 13 of the scope 10. The operating buttons include a freeze button, a copy button, a record button, and so on. Moving pictures are changed to still pictures by manipulating the freeze button. Still pictures are copied by the copy button. When a video printer and a VTR (not shown) are connected to the device 20, still pictures and moving pictures are recorded based on the image signals processed in the device 20, by manipulating these buttons.

A system controller 21 of the image-signal processing device 20 is a micro computer which wholly controls the electronic endoscope. Namely, the system controller 21 has a CPU, a memory (ROM) in which programs for performing a plurality of routines, constants, and so on, are stored, and another memory (RAM), in which data are temporally stored.

When the electronic scope 10 is connected to the image-signal processing device 20, an incident end of the light guide 12 is optically connected to a light source unit 22. The light source unit 22 is provided with a white light source (omitted in FIG. 1), such as a xenon lamp, a halogen lamp, and so on. A light adjusting unit 23 including a diaphragm and a collective lens (omitted in FIG. 1) is situated between the incident end of the light guide 12 and the light source unit 22. The diaphragm adjusts the quantity of luminous flux which is incident in the incident end of the light guide 12. The light, which is emitted from the white light source, is led to the incident end of the light guide 12 by the collective lens. Further, when the scope 10 is connected to the device 20, the CCD image sensor of the imaging sensor 11 is connected to an image processing circuit 24 of the device 20 through a CCD buffer circuit (omitted in FIG. 1).

The image-signal processing device 20 is provided with a front panel (omitted in FIG. 1). The front panel is provided with a plurality of indicating lights and a plurality of switches, such as a power switch and a lighting switch. The ON/OFF status of a main power (omitted in FIG. 1) of the device 20 is controlled by the power switch, and the white light source of the light source unit 22 is controlled by the lighting switch.

The system controller 21 outputs a control signal to a lamp power circuit (omitted in FIG. 1) of the light source unit 22, based on the signal input from the lighting switch. In accordance with the control signal from the system controller 21, the electricity supplied to the white light source is controlled by the lamp power circuit.

After the start of the electricity supply to the white light source, a white illumination light exits from the end surface of the emitting end of the light guide 12, the object of view is illuminated by the white illumination light, and then an optical image of the object is imaged on a receiving plane of the CCD image sensor by the objective optical system of the imaging sensor 11. The image sensor 11 carries out photo-electric conversion of the optical image on the receiving plane, so that the optical image is converted to analog pixel signals for one frame. The analog pixel signals are sequentially read out from the image sensor 11 by a CCD driver 14 provided in the scope 10.

The analog pixel signals are subjected to predetermined image processes in the image processing circuit 24. Next, after the analog pixel signals are converted to video signals for output in an output control unit 25, the video signals are transmitted to the TV monitor 30 through an output terminal 26.

Figure 2:
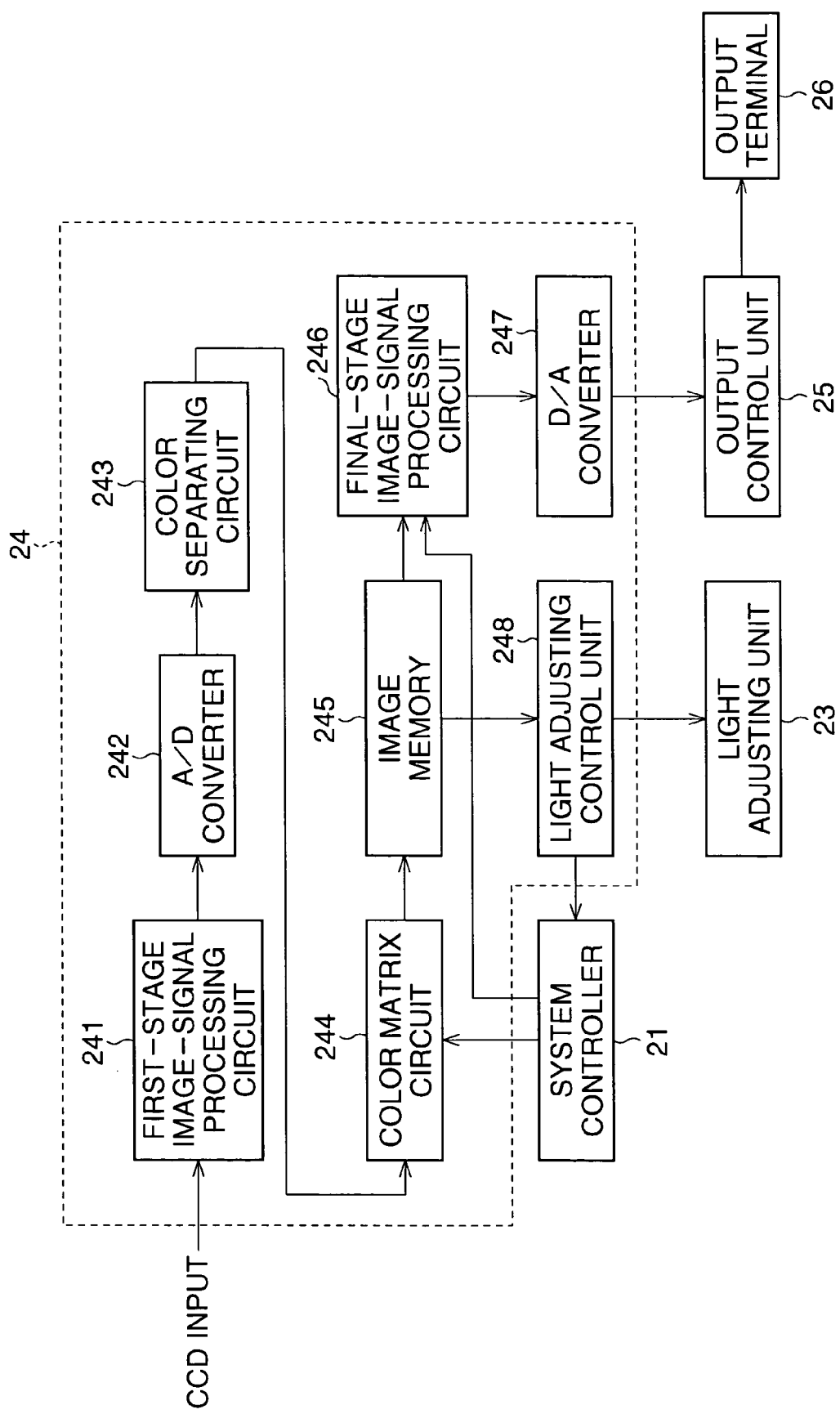
FIG. 2 is a block diagram of an image processing circuit.

FIG. 2 is a block diagram which shows a structure of the image processing circuit 24. The analog pixel signals for one frame, which are read out from the image sensor 11, are input to a first-stage image-signal processing circuit 241. A preamplifier, a band-pass video filter, and so on, are provided in the circuit 241. The input analog signals are subjected to predetermined signal processes such as sample hold, amplification, gamma correction, and so on.

After being subjected to the signal processes in the circuit 241, the analog pixel signals are converted to digital pixel signals by an analog/digital (A/D) converter 242, and the digital pixel signals are input to a color separating circuit 243. In the color separating circuit 243, a color separating operation is carried out on the digital pixel signals which include each of the color component signals of the complementary color chip filters. By this operation, the digital pixel signals are separated to RGB signals which include a red color (R) component signal, a green color (G) component signal, and a blue color (B) component signal. The RGB signals are input from the circuit 243 to a color matrix circuit 244. In the circuit 244, the RGB signals which were separated in the circuit 243 are subjected to a multiplication by a predetermined matrix coefficient. In this operation in the circuit 244, the RGB signals are converted so as to have a proper color balance. After the operation of the circuit 244, the RGB signals are stored in an image memory 245.

The RGB signals which were stored in the image memory 245 are read out to input to a final-stage signal processing circuit 246. The circuit 246 includes a color balance amplifier. By the color balance amplifier, the color balance of the RGB signals is changed based on white balance data which are input from the system controller 21. Further, after the color balance change, the RGB signals are subjected to image processing operations, such as clamping, gamma correction, contour correction, superimposing, and so on. After the image processing operations of the circuit 246, the RGB signals are converted to analog signals by a digital/analog (D/A) converter 247. An output controlling unit 25 includes a cable driver and an encoder. In the unit 25, the video-signal-formatting operation for the analog RGB signals is carried out. After the formatting, the analog RGB signals are transmitted to the TV-monitor 30 through the output terminal 26, as described above. Due to these operations, the picture of the image captured by the color CCD is reproduced on the display of the monitor 30.

Also, the RGB signals stored in the image memory 245 are output to a light adjusting control unit 248. In the unit 248, luminance signals are extracted from the RGB signals. Further, a light adjusting control signal "I" is calculated based on the luminance signals. The picture on the display of the TV-monitor 30 is reproduced based on the image signals obtained from pixels in an effective area of the imaging plane of the CCD image sensor. The signal "I" is obtained by calculating an average value of luminance signals of all pixels which are in the effective area and a peak value of pixels which are in the central portion of the effective area, and weighting each of these values.

The signal "I", which was calculated in the unit 248, is output to the light adjusting unit 23. The unit 23 adjusts the quantity of light which passes through the diaphragm by driving the diaphragm based on the signal "I". Consequently, the quantity of white light, which is output from the light source unit 22 and input to the incident end of the light guide 12, is controlled. Accordingly, the picture of the object image, reproduced on the display of the TV-monitor 30, has the best luminance. Further, the signal "I" is output to the system controller 21 to be used in changing the color matrix coefficient as described later.

Now, the operations in the color separating circuit 243 and the color matrix circuit 244 are explained. The color separation of the RGB signals which are output from the CCD image sensor is performed based on expression (1). Note that, in the expression (1), "R'" is the red color component after the color separation, "G'" is the green color component after the color separation, "B'" is the blue color component after the color separation, "Mg" is the magenta color component output from the CCD image sensor, "Ye" is the yellow color component output from the CCD image sensor, "Cy" is the cyan color component output from the CCD image sensor, and "G" is the green color component output from the CCD image sensor.

$$\left.\begin{array}{l} R' = Mg + Ye - Cy - G \\ G' = Mg - Ye + Cy - G \\ B' = Mg + Ye + Cy + G \end{array}\right\} \quad (1)$$

Also, the converting operation of the RGB signals in the color matrix circuit 244 is performed based on expression (2). In the expression (2), "R'" is the red color component after the color separation, "G'" is the green color component after the color separation, "B'" is the blue color component after the color separation, "R" is the red color component after the color conversion, "G" is the green color component after the color conversion, and "B" is the blue color component after the color conversion. Further, "α" is the color matrix coefficient, and is a 3×3 matrix which has three rows and three columns, as shown in expression (3).

$$\begin{bmatrix} R \\ G \\ B \end{bmatrix} = \alpha \begin{bmatrix} R' \\ G' \\ B' \end{bmatrix} \quad (2)$$

$$\alpha = \begin{bmatrix} a11 & a12 & a13 \\ a21 & a22 & a23 \\ a31 & a32 & a33 \end{bmatrix} \quad (3)$$

The expression (2) of the color conversion is developed as shown in expression (4), based on the expressions (1) and (3).

$$\begin{aligned} \begin{bmatrix} R \\ G \\ B \end{bmatrix} &= \begin{bmatrix} a11 & a12 & a13 \\ a21 & a22 & a23 \\ a31 & a32 & a33 \end{bmatrix} \begin{bmatrix} R' \\ G' \\ B' \end{bmatrix} \\ &= \begin{bmatrix} a11 & a12 & a13 \\ a21 & a22 & a23 \\ a31 & a32 & a33 \end{bmatrix} \begin{bmatrix} Mg + Ye - Cy - G \\ Mg - Ye + Cy - G \\ Mg + Ye + Cy + G \end{bmatrix} \\ &= \begin{bmatrix} (a11+a12+a13)Mg + (a11-a12+a13)Ye + (-a11+a12+a13)Cy + (-a11-a12+a13)G \\ (a21+a22+a23)Mg + (a21-a22+a23)Ye + (-a21+a22+a23)Cy + (-a21-a22+a23)G \\ (a31+a32+a33)Mg + (a31-a32+a33)Ye + (-a31+a32+a33)Cy + (-a31-a32+a33)G \end{bmatrix} \end{aligned} \quad (4)$$

For example, if the color matrix coefficient which is shown in expression (5) is used, an expression (6) can be obtained based on the expression (2) of the color conversion.

$$\alpha = \begin{bmatrix} 3.38 & 0.81 & -0.38 \\ -0.75 & 1.13 & -1.06 \\ -0.38 & 1.06 & 2.06 \end{bmatrix} \quad (5)$$

$$\begin{aligned} \begin{bmatrix} R \\ G \\ B \end{bmatrix} &= \begin{bmatrix} a11 & a12 & a13 \\ a21 & a22 & a23 \\ a31 & a32 & a33 \end{bmatrix} \begin{bmatrix} R' \\ G' \\ B' \end{bmatrix} \\ &= \begin{bmatrix} a11 & a12 & a13 \\ a21 & a22 & a23 \\ a31 & a32 & a33 \end{bmatrix} \begin{bmatrix} Mg + Ye - Cy - G \\ Mg - Ye + Cy - G \\ Mg + Ye + Cy + G \end{bmatrix} \\ &= \begin{bmatrix} (a11+a12+a13)Mg + (a11-a12+a13)Ye + (-a11+a12+a13)Cy + (-a11-a12+a13)G \\ (a21+a22+a23)Mg + (a21-a22+a23)Ye + (-a21+a22+a23)Cy + (-a21-a22+a23)G \\ (a31+a32+a33)Mg + (a31-a32+a33)Ye + (-a31+a32+a33)Cy + (-a31-a32+a33)G \end{bmatrix} \\ &= \begin{bmatrix} 3.81Mg + 4.57Ye - 2.95Cy - 2.19G \\ -0.68Mg + 1.44Ye + 0.82Cy + 2.94G \\ 2.74Mg - 1.38Ye + 3.5Cy - 0.62G \end{bmatrix} \end{aligned} \quad (6)$$

Figure 3:
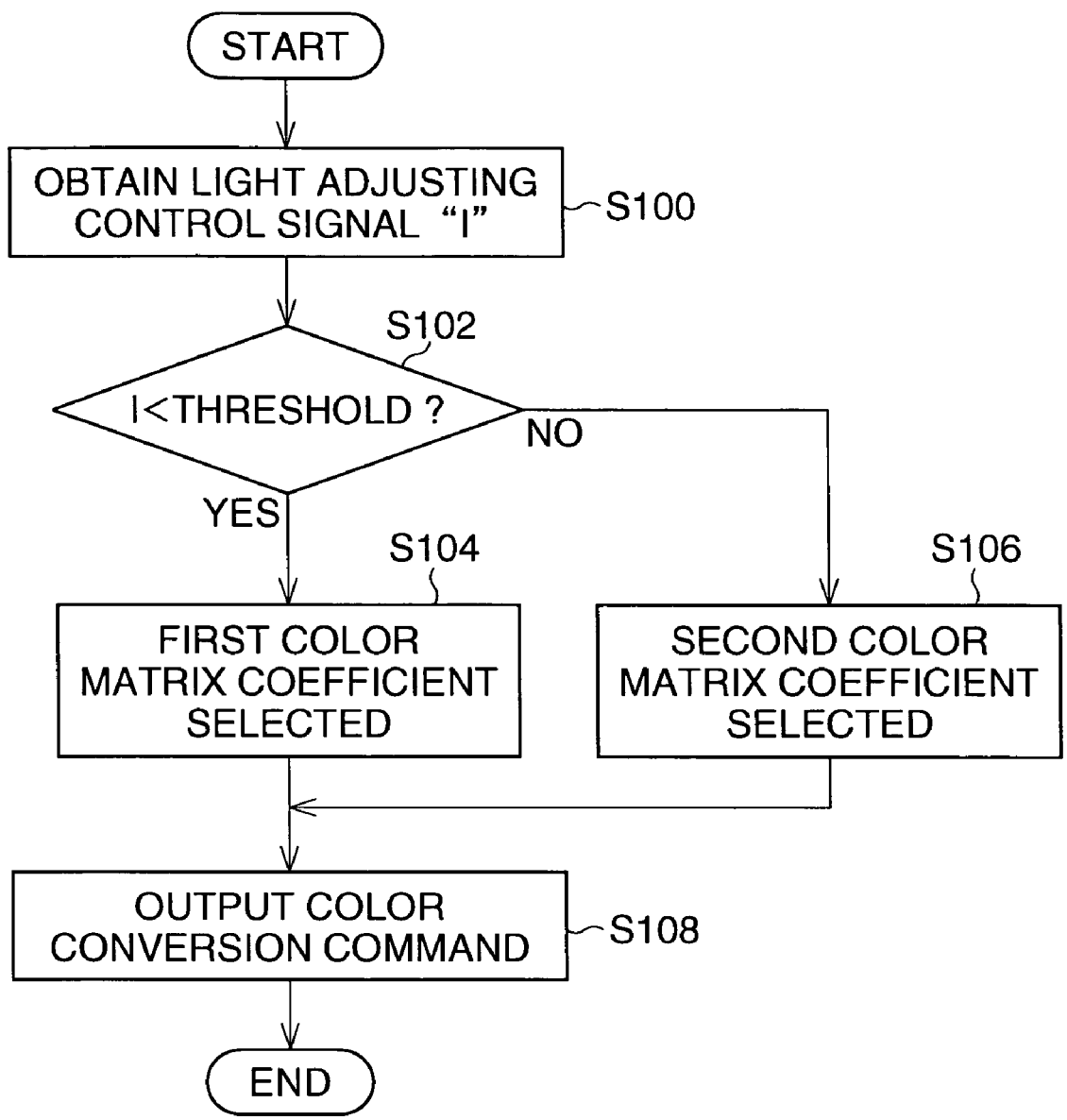
FIG. 3 is a flowchart which shows processes of color conversion in the first embodiment.

In the first embodiment, the color matrix coefficient is selected in accordance with the luminance of the object image. FIG. 3 is a flowchart which shows the procedure of color converting adjustment by the system controller 21.

In step S100, the light adjusting control signal "I" is obtained. In the first embodiment, the color conversion is first carried out using a default color matrix coefficient in the color matrix circuit 244, and then, in the light adjusting control unit 248, the signal "I" is calculated based on the image signals which were subjected to the color conversion. After the signal "I" which is calculated in the unit 248 is input, the control goes to step S102.

In step S102, the signal "I" is compared with a predetermined threshold. The threshold is set to a level, such that it can be judged if the object image is brighter than usual, and the picture that is reproduced on the display of the TV-monitor 30 has high luminance, when the signal "I" is larger than the threshold. For example, the threshold is set to the highest level of luminance at which the object image does not provoke halation. The reason why the threshold is set to this level will be explained later.

When the signal "I" is less than the threshold, namely when the luminance of the object image is not high, the control goes to step S104. In step S104, a first color matrix coefficient is selected. On the other hand, when the signal "I" is not less than the threshold, namely, the luminance of the object image is high, the control goes to step S106. In step S106, a second color matrix coefficient is selected. At least one element of the matrix denoted in expression (3), for example, the element $a21$, is different between the first and second color matrix coefficients. Namely, the first coefficient is set so as to correspond to a standard color condition (normal color condition). And, the second coefficient is set so as to have at least one element different from the corresponding element of the first coefficient, so that the color condition, which is judged in comparison with the threshold to be changed, can be corrected to be the standard condition. Note that, the concrete setting method of the second coefficient will be explained later.

After the color matrix coefficient is selected in steps S104 or S106, the control goes to step S108. In step S108, a control command, which requests the calculation of the above-mentioned expression (2) using the selected coefficient, is output to the color matrix circuit 244.

Note that, in the first embodiment, the signal "I" is calculated based on the average value of luminance signals of all pixels which are in the effective area and the peak value of pixels of the central portion. However, only the peak value can be used for the signal "I".

Further, in the first embodiment, the first color matrix coefficient is the default coefficient. Additionally, it is possible for the signal "I" to be compared with a plurality of thresholds hence a plurality of color matrix coefficients corresponding to the thresholds should prepared; and the color matrix coefficient should be determined for two or more levels.

Figure 4:
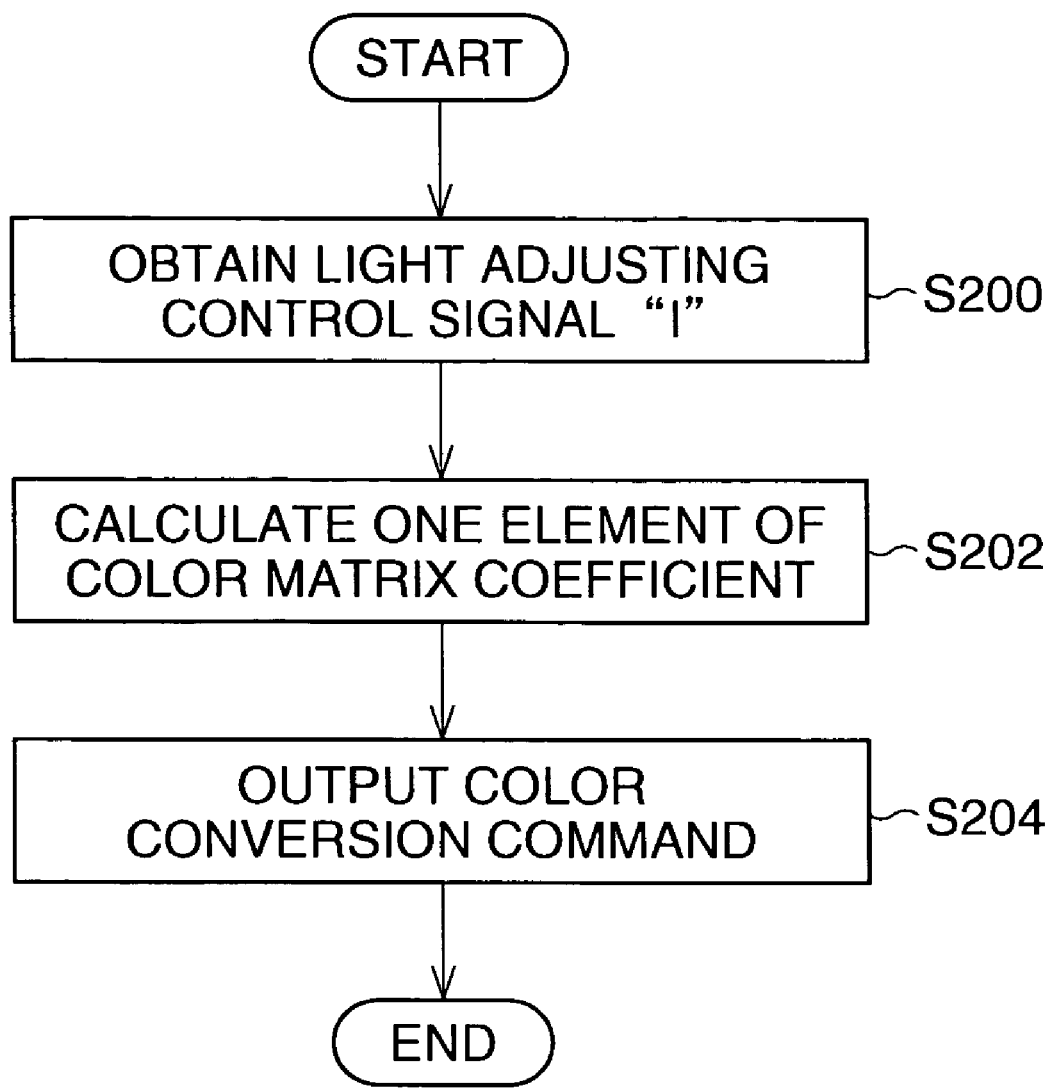
FIG. 4 is a flowchart which shows processes of color conversion in a second embodiment according to the present invention.

FIG. 4 is a flowchart which shows the procedure for color conversion in an electronic endoscope to which a second embodiment according to the present invention is applied. Note that, the electronic endoscope of the second embodiment is provided with device structures identical to those (shown in FIGS. 1 and 2) of the electronic endoscope of the first embodiment.

After the light adjusting control signal "I" is obtained in step S200, the control goes to step S202. In step S202, the value of a predetermined element (for example, the element $a21$ in the second line of the first row) of the color matrix coefficient shown in the above-mentioned expression (3) is calculated. The calculation in step S202 is carried out based on a predetermined expression (for example, "I"÷500−0.75), using the signal "I". The color condition of the object image changes in accordance with the change of the luminance. The predetermined expression of step S202 is determined so as to correct the changed color condition of the object image to be the standard color condition. Next, in step S204, a control command, which requests the RGB signal calculation based on the above-mentioned expression (2) using the coefficient in which the element $a21$ is determined, is output to the color matrix circuit 244. Note that, the calculation for creating the signal "I" is similar to that of the first embodiment.

Figure 5:
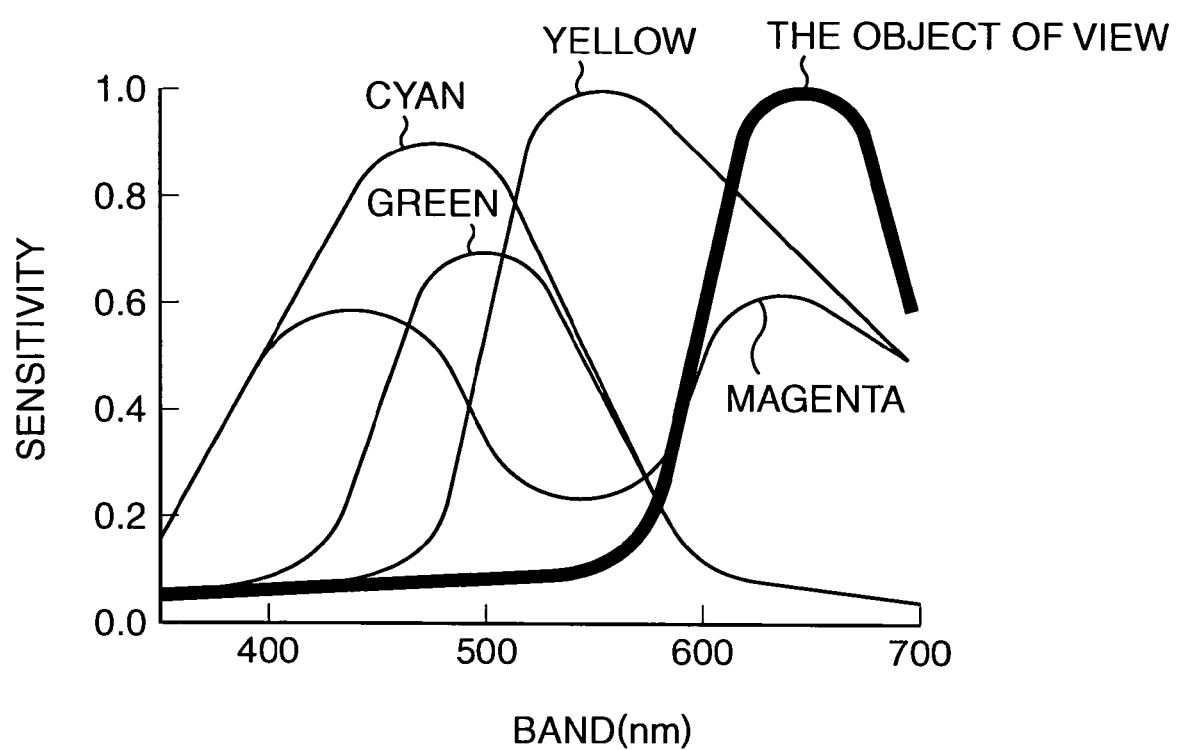
FIG. 5 is a graph which shows spectral sensitivity characteristics of complementary color filters and an object of view.

In FIG. 5, spectral sensitivity characteristics of the complementary color filters of the color CCD used in the CCD image sensor are represented by narrow lines. As is apparent from FIG. 5, the colors (cyan, magenta, yellow, green) of the complementary color filters show characteristics of overlapping at some frequencies. On the other hand, as represented by the wide line in FIG. 5, the color of the inside of a human body (the object of view) includes a lot of red color components. Namely, the color includes a lot of frequency components of 600 through 700 nm (nanometers) Accordingly, information of the red color components is obtained by the CCD image sensor through the complementary color filters of yellow and magenta, which have a sensitivity to light in the range from 600 through 700 nm.

When the object image has the highest level of luminance at which the picture of the object image does not provoke halation, the pixels corresponding to the filters of yellow and magenta saturate, however, the pixels corresponding to the filters of cyan and green do not saturate. In this situation, if the RGB signals are calculated based on the above-mentioned expression (4), the red color of the inside of the body is reproduced as a magenta color which is a little green in color.

In the first embodiment, each value of the elements of the second color matrix coefficient is set so as to be able to precisely reproduce the red color even if the object image has the highest level of luminance at which the picture of the object image does not provoke halation. Further, in the second embodiment, the calculation of one element (for example, the element $a21$) using the signal "I" is defined so as to precisely reproduce the red color in the above-mentioned situation of high luminance.

Note that, in the second embodiment, one element of the color matrix coefficient, for example only the element $a21$ of the secondline of the first row, is changed, in consideration of the calculation speed. However, other elements, which relate to the green color component, namely the element $a22$ of the second row or the second line, the element $a23$ of the third row and the second line, can be changed. Further, a plurality of elements (for example, all three elements which relate to the green color component) can be respectively changed by the corresponding expressions. Similarly, the color conversion may be performed changing the elements relating to the red color component or the elements relating to the blue color component.

According to the present invention, good color reproduction can be carried out at all times in an electronic endoscope which is provided with a color CCD.

The present disclosure relates to subject matter contained in Japanese Patent Application No. 2002-368402 (filed on Dec. 19, 2002) which is expressly incorporated herein, by reference, in its entirety.

The invention claimed is:

1. An electronic endoscope comprising:
   a device that carries out photoelectric conversion of an image of an object of view and outputs pixel signals of said object image;
   a converter that converts said pixel signals to color component signals for video signals;
   a color adjuster that adjusts colors of said color component signals by multiplying the color component signals by a predetermined matrix coefficient;
   a light adjusting controller that calculates a luminance of said object image from said color component signals, the colors of which are adjusted, and creates a control signal for adjusting the quantity of illumination light based on said calculated luminance of said object image;
   a color adjusting controller that changes said predetermined matrix coefficient based on said control signal and based on spectral sensitivity characteristics of complementary color filters provided in said device.

2. An electronic endoscope according to claim 1, wherein said color adjusting controller compares said control signal with a predetermined threshold, and selects one matrix coefficient from a plurality of matrix coefficients based on said comparison, said plurality of matrix coefficients having at least one different element.

3. An electronic endoscope according to claim 1, wherein said color adjusting controller changes at least one element of said predetermined matrix coefficient based on a predetermined expression using said control signal.

4. An electronic endoscope according to claim 1, wherein said light adjusting controller obtains said control signal by calculating an average value of luminance of all pixels which compose said object image and a peak value of luminance of pixels which are in the central portion of said object image.

5. An electronic endoscope according to claim 4, wherein said light adjusting controller weights each of said average values and said peak value.

6. An electronic endoscope according to claim 3, wherein said color adjusting controller changes a plurality of elements, of said predetermined matrix coefficient, which relate to one color component.

7. An electronic endoscope according to claim 3, wherein said color adjusting controller changes a plurality of elements, of said predetermined matrix coefficient, which relate to a plurality of color components.

* * * * *